US012766282B2

(12) United States Patent
Helleis

(10) Patent No.: US 12,766,282 B2
(45) Date of Patent: Oct. 20, 2026

(54) VENTILATION APPARATUS FOR VENTILATING A PERSON, CONTROL METHOD FOR CENTRIFUGAL FAN OF A VENTILATION APPARATUS, AND VENTILATION METHOD

(71) Applicant: MAX-PLANCK-GESELLSCHAFT ZUR FÖRDERUNG DER WISSENSCHAFTEN E.V., Munich (DE)

(72) Inventor: Frank Helleis, Mainz (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 728 days.

(21) Appl. No.: 18/016,736

(22) PCT Filed: Jul. 19, 2021

(86) PCT No.: PCT/EP2021/070158
§ 371 (c)(1),
(2) Date: Feb. 23, 2023

(87) PCT Pub. No.: WO2022/018031
PCT Pub. Date: Jan. 27, 2022

(65) Prior Publication Data

US 2023/0310777 A1 Oct. 5, 2023

(30) Foreign Application Priority Data

Jul. 20, 2020 (DE) ..................... 10 2020 119 085.9

(51) Int. Cl.
*A61M 16/00* (2006.01)
*A61M 16/10* (2006.01)
*A61M 16/20* (2006.01)

(52) U.S. Cl.
CPC .... *A61M 16/0066* (2013.01); *A61M 16/0069* (2014.02); *A61M 16/024* (2017.08);
(Continued)

(58) Field of Classification Search
CPC .......... A61M 16/0066; A61M 16/0069; A61M 16/024; A61M 16/106; A61M 16/1065;
(Continued)

(56) References Cited

U.S. PATENT DOCUMENTS

2002/0057967 A1* 5/2002 Eimer ............... A61M 16/0057 415/206
2004/0216740 A1* 11/2004 Remmers ............ A61M 16/085 128/204.18
(Continued)

FOREIGN PATENT DOCUMENTS

CN 102695536 A 9/2012
CN 108430555 A 8/2018
(Continued)

OTHER PUBLICATIONS

International Search Report for PCT/EP2021/070158 Dated Nov. 10, 2021.
(Continued)

*Primary Examiner* — Joseph D. Boecker
(74) *Attorney, Agent, or Firm* — Grogan, Tuccillo & Vanderleeden LLP

(57) ABSTRACT

An apparatus comprises a centrifugal fan having an inlet and outlet, the fan receives ventilation air at the inlet and provides the ventilation air at an adjustable pressure at the outlet, a first respiration line with a first end connected to the inlet and a second end for receiving inhalation air, a second respiration line having a first end connected to the outlet and a second end for coupling a filter and a ventilation mask, the second respiration line having a sensor, to measure a flow
(Continued)

parameter in the second respiration line, and a device for controlling the fan according to an output signal of the sensor, the fan and second respiration lines forming a continuous bidirectional flow path, the adjustable ventilation pressure at the outlet comprises an inhalation or an exhalation pressure less than or equal to the inhalation pressure, and the second respiration line has an air filter.

18 Claims, 3 Drawing Sheets

(52) U.S. Cl.
CPC .......... *A61M 16/106* (2014.02); *A61M 16/20* (2013.01); *A61M 2016/0027* (2013.01); *A61M 2016/0036* (2013.01); *A61M 16/0051* (2013.01); *A61M 16/1065* (2014.02); *A61M 16/107* (2014.02); *A61M 16/1075* (2013.01); *A61M 16/208* (2013.01)

(58) Field of Classification Search
CPC ............ A61M 16/107; A61M 16/1075; A61M 16/1095; A61M 16/20; A61M 16/208; A61M 2016/0027; A61M 2016/0039
See application file for complete search history.

(56) References Cited

U.S. PATENT DOCUMENTS

| | | | | |
|---|---|---|---|---|
| 2005/0039749 | A1* | 2/2005 | Emerson | A61M 16/0009 128/204.23 |
| 2015/0120067 | A1* | 4/2015 | Wing | H02J 7/00308 700/282 |
| 2018/0064894 | A1 | 3/2018 | Fu et al. | |
| 2019/0269871 | A1* | 9/2019 | Kenyon | F04D 29/281 |

FOREIGN PATENT DOCUMENTS

| | | | |
|---|---|---|---|
| CN | 108626144 | A | 10/2018 |
| CN | 208281234 | U | 12/2018 |
| CN | 109922856 | A | 6/2019 |
| DE | 200 16 769 | | 12/2000 |
| DE | 10 2008 005 558 | | 7/2009 |
| DE | 10 2008 047 026 | | 3/2010 |
| DE | 10 2018 003 027 | | 10/2019 |
| JP | 2018 531716 | | 11/2018 |
| WO | 2009112076 | | 9/2009 |
| WO | 2018204985 | | 11/2018 |

OTHER PUBLICATIONS

Galbiati et al., "Mechanical Ventilator Milano (MVM): A Novel Mechanical Ventilator Designed for Mass Production in Response to the COVID-19 Pandemic", arXiv:2003.10405 [physics.med-ph] Apr. 10, 2020.

Chinese Office Action for Chinese Application No. 202180062983.X, issued Jul. 25, 2026, 8 pages.

* cited by examiner

VENTILATION APPARATUS FOR VENTILATING A PERSON, CONTROL METHOD FOR CENTRIFUGAL FAN OF A VENTILATION APPARATUS, AND VENTILATION METHOD

FIELD OF THE INVENTION

The invention relates to a ventilation apparatus which is adapted for the artificial, non-invasive (NIV) ventilation of a person, and in particular contains a centrifugal fan. The invention furthermore relates to a control method for controlling a centrifugal fan for ventilating a person, in particular for controlling a centrifugal fan in the ventilation apparatus, and to a method (ventilation method) for operating the ventilation apparatus. Applications of the invention are found in medicine with non-invasive ventilating of patients.

BACKGROUND OF THE INVENTION

In ventilating technology, various types of ventilation devices are known, which differ with respect to their configurations and modes of operation (see e.g. DE 10 2008 047 026 B4, WO 2009/112 076 A1, DE 10 2008 005 558 A1 and DE 10 2018 003 027 A1). The ventilation pressure of a ventilation gas can be generated in a ventilation apparatus for example by connection to a pressurized gas reservoir (see e.g. C. Galbiati et al., 2020, arXiv:2003.10405) or by means of a fan. A centrifugal fan can be used as the fan (see e.g. DE 200 16 769 U1), which has advantages on account of its compact design.

Typically, BIPAP (Biphasic Positive Airway Pressure) ventilation is performed with modern ventilation devices, i.e. a pressure-controlled method in which ventilation is carried out using two different pressure levels, which are in each case adjusted upon inhalation (inspiration) or exhalation (expiration). Compared with the older volume-controlled methods, pressure-controlled methods inherently have the main advantage, without additional outlay, of assisting the patient in their spontaneous breathing attempts during the weaning-off phase. Important ventilation parameters are thus in particular the positive end-expiratory pressure (PEEP), which denotes the positive pressure in the lungs at the end of the exhalation (expiration), and the maximum pressure which occurs during inhalation (inspiration) (peak pressure or Ppeak or PIP).

With a plurality of conventional ventilation devices, these pressure levels are adjusted by means of (proportional) valves, which, however, by nature do not control the pressure itself, but rather the flow, which leads to the desired pressure only in combination with the patient's lung volume. In the case of one-hose systems for example, the exhalation air can be removed, in order to minimise the $CO_2$ rebreathing, close to the ventilation mask, by means of a controlled leak, a passive differential pressure-controlled valve, or an active proportional valve. In the case of two-hose systems, active components can be integrated into the control device, with the additional disadvantage of even higher costs.

However, the extremely high complexity of apparatus (valves, hoses, additional filters for protecting the surroundings), sensors (double flow measurement) and algorithms (safety devices in the case of power failure or malfunction), and thus significantly higher costs or a lack of important diagnostic options such as the exhalation volume or the determination of a mask leak are disadvantageous. If for example mask leaks could be diagnosed online and were small enough, the respiration air could be temperature-controlled and humidified by simple HME (heat-moisture exchange) filters, which would eliminate further apparatus outlay for respiration air conditioning in the event of resource scarcity.

Conventional ventilation apparatuses, in particular for intensive care purposes, are thus typically high-cost, complex devices, which are in each case adapted specifically for the requirements of a particular use, such as in a clinic or in an emergency vehicle. The operation of conventional ventilation devices generally requires incorporation into existing intensive care technology, and operation and monitoring by specialist staff.

On account of lung diseases occurring as a pandemic, such as the Covid-19 outbreak in 2020, there is a need for ventilation devices with lower cost, and which are of minimum technical complexity, use a minimum of clinical resources, and have the widest possible field of use.

SUMMARY OF THE INVENTION

The objective of the invention is that of providing an improved ventilation apparatus comprising a centrifugal fan, by means of which disadvantages of conventional techniques can be avoided. The ventilation apparatus is intended in particular to be of a simplified design, without functional limitation during use, to be able to be manufactured at lower cost, to have a reduced power consumption, to be operable as independently of further devices as possible, to be operable in an automated manner, and/or to be easily operable. The objective of the invention is furthermore that of providing an improved control method for controlling a centrifugal fan of a ventilation apparatus, and a method for operating a ventilation apparatus, by means of which disadvantages of conventional techniques are avoided. The control method and the operation of the ventilation apparatus should take place as far as possible independently of further peripheral devices, and/or in a manner having increased reliability in different operating phases of the ventilation apparatus. The control method should in particular be standardised.

These objectives are achieved, respectively, by a ventilation apparatus and a method which comprise the features of the independent claims. Preferred embodiments and applications of the invention can be found in the dependent claims.

According to a first general aspect of the invention, the above objective is achieved by a ventilation apparatus which is adapted for non-invasive ventilation of a person.

The ventilation apparatus comprises a centrifugal fan having an inlet opening and an outlet opening. The centrifugal fan is adapted to receive ventilation air at the inlet opening and to provide the ventilation air at an adjustable ventilation pressure at the outlet opening. The ventilation pressure is preferably adjustable by adjusting the power of the centrifugal fan, in particular the rotational speed of the centrifugal fan. Different ventilation pressures are adjustable in different respiration phases.

The ventilation apparatus further comprises a first respiration line (or: periphery-side respiration line) having a first end connected to the inlet opening of the centrifugal fan, and having a second end arranged for receiving inhalation air. The ventilation apparatus further comprises a second respiration line (or: patient-side respiration line) having a first end connected to the outlet opening of the centrifugal fan, and having a second end adapted for coupling a ventilation mask. The second end of the second respiration line is preferably provided with a coupling device which is adapted for connection to the ventilation mask. Alternatively, the second end of the second respiration line is rigidly connected to the ventilation mask. The face mask can be a part of the ventilation apparatus. The ventilation mask is a face mask which can be fixed to the face of a person to be ventilated. Preferably a ventilation mask is provided which is not additionally ventilated and which comprises a face mask that sits in an airtight manner on the face of the ventilated person, such that, in the case of undisturbed operation and correct fit, the person breathes exclusively via the patient-side respiration line, and no or a negligibly small amount of air enters or escapes at the sides.

The second respiration line is provided with a sensor device, by means of which at least one flow parameter in the second respiration line can be measured. A control device of the ventilation apparatus, preferably at least one microprocessor circuit, is provided for controlling the centrifugal fan in dependency on at least one output signal of the sensor device.

According to the invention, the centrifugal fan and the second respiration line form a continuous bidirectional flow path, i.e. a flow path having two alternative flow directions. The centrifugal fan and the second respiration line are adapted for opposing flow directions, in each case in the different breathing phases, in particular in the inhalation phase and in the exhalation phase. Optionally the first respiration line or at least a part thereof up to an optionally provided valve device is also part of the continuous bidirectional flow path. The flow directions comprise a first flow direction from the second end of the first respiration line, via the centrifugal fan, to the second end of the second respiration line (inhalation phase), or a second flow direction from the second end of the second respiration line, via the centrifugal fan, to the second end of the first respiration line (exhalation phase), or optionally to an expiration valve between the centrifugal fan and the first end of the first respiration line. The adjustable ventilation pressure at the outlet opening of the centrifugal fan is an inhalation pressure or an exhalation pressure which is equal to or less than the inhalation pressure.

The inventor has found that the exhalation can take place via the centrifugal fan and counter to the operating pressure of the centrifugal fan, which makes it possible to provide the bidirectional flow path. The bidirectional flow path offers the advantage that the design of the ventilation apparatus is significantly simplified compared with conventional techniques. The patient-side respiration line can comprise a single respiration line, via which the ventilation apparatus is connected to the ventilation mask. Providing the bidirectional flow path furthermore allows for simplified sensors. All the flow parameters necessary for controlling the ventilation apparatus can be acquired by means of the sensor device concentrated locally on the second respiration line, as a result of which the control of the ventilation apparatus is simplified.

Furthermore, according to the invention, the second respiration line is provided with a filter device which is arranged for air flow filtering. The filter device comprises a filter, preferably a HEPA filter, via which the flow passes through into the second respiration line. Advantageously, the filter device fulfils a dual function, by providing the bidirectional flow path. Firstly, the surroundings are protected against germs which could possibly escape from the patient, and secondly the patient is protected against germs which could possibly migrate in from the surroundings. Providing a single filter device, preferably having a single filter, further simplifies the design and the operation of the ventilation apparatus.

Advantageously, the centrifugal fan can be miniaturised, such that the ventilation apparatus according to the invention provides a system which is easy to produce and is capable of implementing an automatable ventilation process with minimal technical outlay (preferably ventilation mask, HEPA filter and microprocessor-controlled centrifugal fan), having a diameter of less than or equal to 10 cm, preferably less than or equal to 7 cm, and a mass of less than or equal to 100 g, preferably less than or equal to 60 g. Furthermore, an extremely low power consumption of for example approximately 12 W can be made possible, which allows for longer operation on a battery, such as a vehicle battery, in order to be able to maintain the functionality even in the event of unstable electricity supply, e.g. under disaster conditions.

According to a second general aspect of the invention, the above objective is achieved by a control method for controlling a centrifugal fan for ventilating a person. The control method comprises the steps of controlling the centrifugal fan using a first control loop, by means of which a ventilation pressure at an outlet opening of the centrifugal fan can be adjusted to an inhalation pressure or to an exhalation pressure which is equal to or less than the inhalation pressure, and controlling the centrifugal fan using a second control loop, by means of which at least one of the following can be adjusted: a frequency of inhalation phases, in which the inhalation pressure is established at the outlet opening of the centrifugal fan, and a duty cycle of the duration of the inhalation phases relative to the duration of exhalation phases, in which the exhalation pressure is established at the outlet opening of the centrifugal fan.

The control of the centrifugal fan comprises the adjustment of a time function of the fan rotational speed of the centrifugal fan. The control method comprises, with the implementation of the two control loops, a control method which adjusts predetermined flow parameters (target values) on the basis of output values of the sensor device (actual values), in order to obtain the mentioned variables of inhalation pressure, exhalation pressure and frequency of inhalation phases and/or duty cycle of the duration of the inhalation phases relative to the duration of exhalation phases. The centrifugal fan of the ventilation apparatus according to the first general aspect of the invention or an embodiment thereof is preferably controlled by means of the control method or an embodiment thereof.

According to a third general aspect of the invention, the above objective is achieved by a method for operating a ventilation apparatus according to the first general aspect of the invention or one of its embodiments, the method comprising the steps of operating the centrifugal fan, measuring at least one flow parameter by means of the sensor device, and controlling the centrifugal fan by means of a control method according to the second general aspect of the invention or an embodiment thereof. With the method for operating the ventilation apparatus, preferably a ventilation method for ventilating a person who is wearing a face mask coupled to the ventilation apparatus is protected.

The inventor has found that the control of the centrifugal fan makes it possible to fulfil all the desired functions of a ventilation apparatus and, by means of the control method and the ventilation method, to continuously cover the entire spectrum between simple spontaneous breathing, via spontaneous breathing assistance, into the region of purely automatic ventilation in the case of complete respiratory insufficiency. The ventilation pressure generated by the ventilation apparatus advantageously does not depend, or depends to a negligible extent, on the flow (amplitude and/or direction), so that the patient's bidirectional spontaneous breathing is on the one hand not impeded, and on the other hand can be easily detected by a flow change. On this condition, simple indicators also result in order to be able to synchronise the ventilation apparatus to the patient's spontaneous breathing (so-called open system).

Advantageously, the tidal volume or minute volume of the breathing can be adapted by setting the ventilation pressure (inspiration pressure) (IPAP) and the ventilation frequency (f) or the inspiration/expiration ratio (I:E ratio). Typical upper limit values are e.g. IPAP<30 mbar, f<25/min and I:E<1.

The sensor device in the second respiration line advantageously makes it possible to in particular measure the pressure, as the innermost reference variable of the mentioned control loops, at a high degree of accuracy (better 0.5 mbar) and furthermore to measure the flow speed at a high degree of accuracy (better +/−0.2 l/min).

According to a preferred embodiment of the invention, the flow path between the second end of the second respiration line and the inlet opening of the centrifugal fan is free of valves. The flow path along the second respiration line is in particular free of branching. This advantageously makes it possible for the ventilation apparatus to be constructed without a twin hose and without an expiration valve between the face mask and the centrifugal fan, as a result of which the hose volume of the second respiration line, in particular between the filter device and the centrifugal fan, and accordingly the rebreathing of $CO_2$, can be minimised.

According to a further preferred embodiment of the invention, the first respiration line has a valve device, in particular a passive differential pressure-controlled outlet valve or an actively actuatable three-way valve, between the inlet opening of the centrifugal fan and the second end of the first respiration line. The valve device is arranged as an expiration exit for the outlet of exhalation air. Advantageously, a simple passive expiration valve can be arranged in the first respiration line, particularly preferably immediately before the first end of the first respiration line (suction inlet of the centrifugal fan). A passive expiration valve is an exhalation valve which opens into the surroundings in the case of an internal exhalation pressure in the first respiration line which is above atmospheric pressure, and a flow direction towards the outlet, and is otherwise closed, such as a differential pressure-controlled film valve. The suction inlet of the centrifugal fan is thus advantageously switched automatically, depending on the direction of the airflow flowing through the centrifugal fan, between the inlet for the supply of oxygen (optionally with humidification) and the expiration exit. Thus, a particularly simple separation of inspiration and expiration air is provided. The passive automatic switching is determined in particular by the flow resistance of the first airway line and a respiration air conditioning device which is optionally provided.

Advantageously various possibilities exist for receiving respiration air for the patient via the first respiration line. According to a first variant, the second end of the first respiration line can open into surroundings of the ventilation apparatus. Thus, the structure of the ventilation apparatus is advantageously particularly compact and lightweight. Alternatively or in addition, according to a second variant, the second end of the first respiration line can be adapted for coupling to a respiration air reservoir, such as a compressed air cylinder having a pressure reducing valve. In this case, advantages result from the defined supply of respiration air having a predetermined oxygen percentage, up to pure oxygen.

According to a further embodiment of the invention, a respiration air conditioning device is advantageously coupled to the second end of the first respiration line. The respiration air conditioning device is a component which adjoins the interior of the first respiration line and which adjusts the composition and/or physical properties of the respiration air flowing in the first respiration line by means of physical and/or chemical interaction. The respiration air conditioning device is preferably adapted for adjusting at least one of the parameters moisture, temperature and oxygen content of the inhalation air. For this purpose, the respiration air conditioning device preferably comprises a controllable supply unit for introducing water vapour or aqueous aerosol, optionally mixed with pharmaceutical active agents, a temperature control device (heating and/or cooling device), e.g. based on a resistance heating element and/or a Peltier element, or a controllable supply unit for introducing oxygen. The respiration air conditioning device can for example comprise an evaporation system having a sterile water supply from single-use pouches, as is known in the clinical field from infusion technology, or a commercially available humidifier unit.

The respiration air conditioning device offers the advantage that the acceptance of ventilating and the wellbeing of the patient can be increased if the respiration gas is humidified and/or temperature controlled, in particular if the patient already breathes as by reflex substantially through the mouth in the event of sensed breathlessness. The function of an HME filter, which is insufficient in the case of a conventional ventilation apparatus, can be fulfilled by the respiration air conditioning device. The temperature control can comprise heating of the respiration lines and of the centrifugal fan by means of the temperature-controlled respiration air to at least 30° C., preferably at least 35° C., up to a physiologically acceptable temperature. This advantageously prevents condensate and germ formation in the system after the humidification.

The temperature control device can be adapted for direct temperature control of the respiration air and/or for direct temperature control of the ventilation apparatus, in particular the second respiration line. The temperature control of the ventilation apparatus particularly effectively prevents the formation of condensate and germs.

If, according to a further variant of the invention, the filter device comprises a plug connection to the centrifugal fan and/or the second respiration line, advantages result for the use of the ventilation apparatus, in particular for a simple filter change. After use with a patient, the ventilation apparatus can be easily prepared for a new patient by changing the filter and disinfecting the remaining parts. The plug connection can be lockable, e.g. comprise a bayonet closure, in order to prevent inadvertent separation of the parts of the ventilation apparatus.

According to an advantageous embodiment of the invention, the control device is provided with an interface for receiving an output signal of an oxygen saturation sensor. An oxygen saturation sensor is preferably rigidly connected to the ventilation apparatus. Alternatively, a separate oxygen saturation sensor of a peripheral device can be used. The oxygen saturation sensor is a chemical and/or optical sensor which is known per se and by means of which the oxygen saturation (SpO2) in the blood of the ventilated patient can be measured as the central reference variable.

The control device is preferably arranged directly adjoining the centrifugal fan. If the control device is in particular positioned directly on the centrifugal fan, the interfaces to the sensor device and to actuators of the ventilation apparatus are advantageously minimised.

In addition to the control function, the control device can advantageously fulfil an alarm function and in particular be adapted for outputting an alarm signal in the event of a malfunction of the ventilation apparatus and/or a critical state of the ventilated person being identified. The alarm signal can for example comprise a light signal and/or an acoustic signal and/or a digital alarm (alarm signal which is transmitted via a network connection to a central monitoring computer). The alarm signal can in particular signal to the clinicians when there is a risk of ventilation destabilising.

The control device contains in particular a motor controller, such as a BLDC controller, which is preferably arranged directly on the motor, in order to minimise electromagnetic disturbances in the surroundings.

According to a further advantageous embodiment of the invention, the control device of the ventilation apparatus is adapted for controlling the centrifugal fan using a first control loop (innermost control loop), by means of which the ventilation pressure at the outlet opening of the centrifugal fan can be adjusted. The first control loop forms a pressure control. If the centrifugal fan, according to a preferred variant, has a flat characteristic curve, the ventilation pressure is proportional to the square of the rotational speed of the centrifugal fan. The ventilation pressure has an infinitesimal or negligible dependency on the flow speed, such that the first control loop preferably comprises a PI controller having two learnt I levels for PIP and PEEP as target values.

Furthermore, the control device is preferably adapted for controlling the centrifugal fan using the second control loop, by means of which at least one of the following can be adjusted: a frequency of inhalation phases, in which the inhalation pressure is established at the outlet opening of the centrifugal fan, and a duty cycle of the duration of the inhalation phases relative to the duration of exhalation phases, in which the exhalation pressure is established at the outlet opening of the centrifugal fan. The next highest control level above the first control loop is thus formed by a time control, the target values of which for frequency (f) and duty cycle (I:E) are adjusted and parameterisable within the physiologically reasonable limits. The second control loop predetermines the switching timepoints for the pressure control in the first control loop. The second control loop preferably also contains an adjustment function, in order to synchronise the operation of the centrifugal fan to the spontaneous breathing attempts of the patient.

According to a particularly preferred embodiment of the invention, the control device is additionally adapted for controlling the centrifugal fan using a third control loop, by means of which target variables of the first and/or of the second control loop are adjustable in such a way that the tidal volume and/or the minute volume of the ventilation are matched to predetermined reference variables of the tidal volume and/or of the minute volume. The physiologically predetermined reference variables are targeted by the control using the third control loop, i.e. the tidal volume and the minute volume are adjusted to the reference variables of the tidal volume and of the minute volume, respectively, or are at least approximated thereto. The third control loop forms a further control level, by means of which it is advantageously possible to react to changes in the stiffness of the lungs (compliance) and the airway resistance (resistance) within predetermined, parameterisable limits. The reference variable of the third control loop is the tidal volume which is calculated by the temporal integration of the flow during inspiration and expiration phases. The target value for this controller is given by the minute volume parameter, which can be acquired using the sensor device. The output of the third control loop modifies the target value specifications of the pressure control and the time control. This results in indirectly volume-controlled ventilating, as is provided in the ventilation methods MMV (Mandatory Minute Volume) and Dräger AutoFlow, without the potentially damaging side-effects of conventional direct volume control methods.

Particularly preferably, the control device is furthermore adapted for controlling the centrifugal fan according to an output signal of an oxygen saturation sensor using a fourth control loop, by means of which a target variable of the third control loop is adjustable such that the oxygen saturation in the blood of the ventilated person is matched to a predetermined oxygen saturation reference variable. The oxygen saturation reference variable is physiologically predetermined and is targeted by the control using the fourth control loop, i.e. the oxygen saturation is adjusted to the oxygen saturation reference variables, or is at least approximated thereto. At this highest control level, the target value of the minute volume is specified by an i-controller, which has the oxygen saturation as the reference variable and compares this with its local target value. This advantageously closes the overall control system.

DESCRIPTION OF THE DRAWINGS

Further details and advantages of the invention will be described in the following, with reference to the accompanying drawings. The drawings, schematically in each case, show.

DETAILED DESCRIPTION

Features of preferred embodiments of the invention are described by way of example in the following, with reference to a design of the ventilation apparatus in a spherical housing, a flow diagram of the ventilation apparatus, and a flow diagram of the control loops which are preferably provided. It is emphasized that the implementation of the invention in practice is not limited to the examples shown, but rather can be modified in particular with respect to the dimensions, shapes, materials and design of the control loops.

Figure 1:
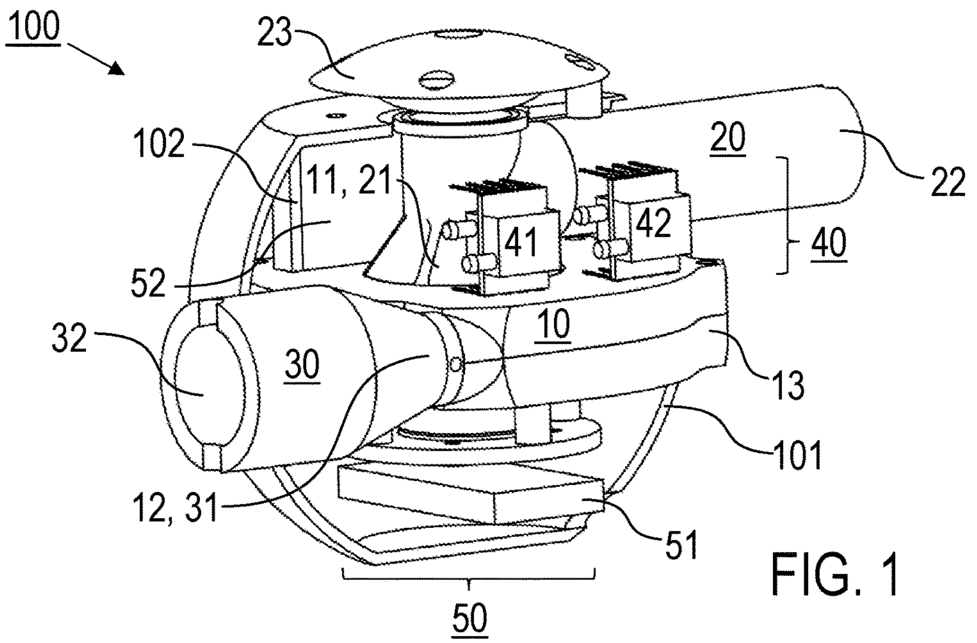
FIG. 1 is a perspective view of a preferred embodiment of the ventilation apparatus according to the invention.
Figure 2:
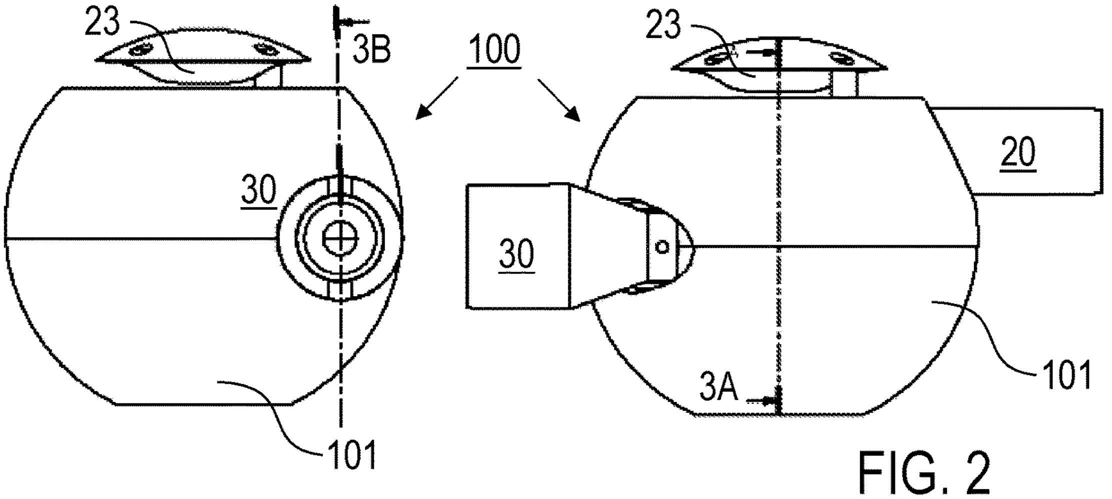
FIG. 2 depicts side views of the ventilation apparatus according to FIG. 1.
Figure 3:
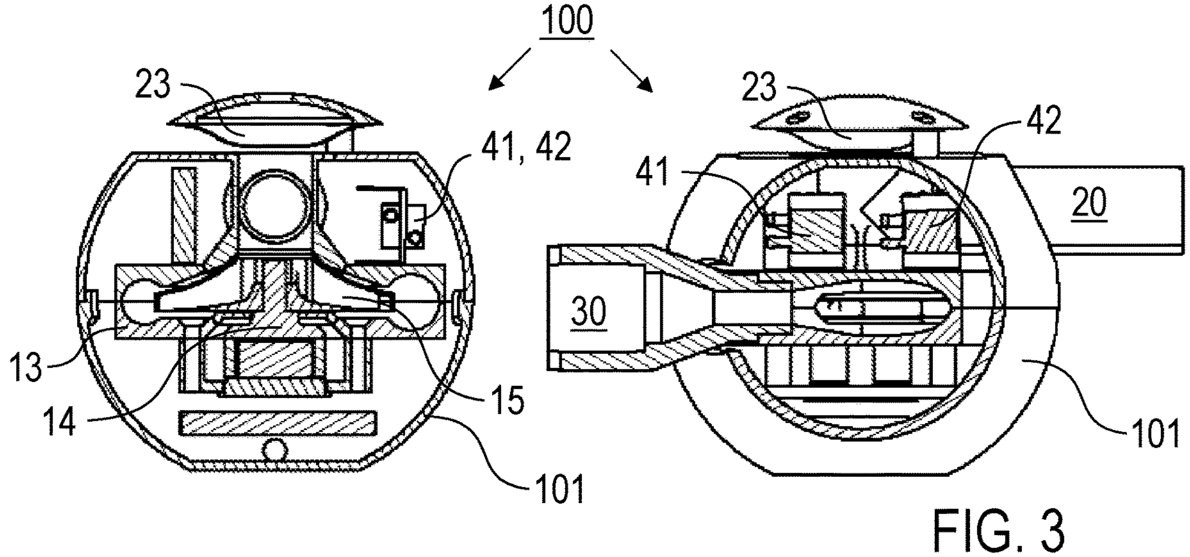
FIG. 3 depicts sectional views of the ventilation apparatus along the lines 3A and 3B in FIG. 2.

An embodiment of the ventilation apparatus 100 is shown schematically in a perspective view in FIG. 1 and in side and sectional views in FIGS. 2 and 3, comprising the centrifugal fan 10, the first respiration line 20 (shown in part), the second respiration line 30 (shown in part), the sensor device 40, and the control device 50, in a substantially spherical housing 101. In a manner known per se, the centrifugal fan 10 contains, in a fan housing 13, an electric motor 14 and an impeller having fan blades 15 (see FIG. 3A). The electric motor 14 is for example a brushless direct current motor (BLDC motor). The axis of rotation of the electric motor 14 define a main axis (z-direction) of the ventilation apparatus 100. The fan housing 13 extends perpendicularly to the main axis, and comprises a central inlet opening 11 which opens along the main axis, and a tangential outlet opening 12 which opens perpendicularly to the main axis. The first end 21 of the first respiration line 20 is connected to the inlet opening 11, and the first end 31 of the second respiration line 30 is connected to the outlet opening 12.

During operation of the centrifugal fan 10, ventilation air is sucked in via the inlet opening 11 and provided at the outlet opening 12 at a ventilation pressure dependent on the respiration phase. The centrifugal fan 10 is preferably provided with straight, radially extending fan blades 15, wherein the centripetal effect of the fan blades 15, and no aerodynamic effects, preferably is used for pressure build-up. Particularly preferably, the fan blades 15 are slanted with respect to the peripheral direction of the centrifugal fan. This reduces the effectiveness, but also the operating noise, of the fan. In the case of a maximum rotational speed, given by the operating voltage, of 40,000 rotations/min, for example a maximum ventilation pressure of approximately 35 mbar is generated at a flow of at most approximately 100 l/min.

The first respiration line 20 and the second respiration line 30 are each formed of a rigid or flexible line material and preferably each comprise a plastics tube. The second end 22 of the first respiration line 20 is connected to the respiration air conditioning device 70 and arranged for receiving inhalation air (see FIG. 4). The second end 32 of the second respiration line 30 is connected to the face mask 110 via a filter device 60 (see FIG. 4).

The valve device 23, comprising a passive outlet valve, is provided at the second end 22 of the first respiration line 20, directly at the inlet opening 11 of the centrifugal fan 10. The valve device 23 closes in the inhalation phases, such that inhalation air is supplied to the centrifugal fan 10, and it opens in the case of an increased pressure in exhalation phases, such that exhalation air is diverted past the first respiration line 20 and into the surroundings. The outlet valve is preferably a simple expiration valve, which is located directly in front of the inlet opening of the fan 11. The inlet opening of the fan 11 is thus switched between oxygen/humidification and expiration exit, depending on the sign of the airflow flowing through the centrifugal fan 10.

The sensor device 40 comprises a pressure sensor 41 and a flow sensor 42, by means of which the pressure or the flow speed in the second respiration line 30 can be acquired. The measurement takes place at a narrowing 43 in the second respiration line 30 (see FIG. 4). The narrowing 43 comprises e.g. a nozzle. The pressure sensor 41 and the flow sensor 42 are connected to the control device 50, which controls the centrifugal fan 10 according to output signals of the sensors, as is described below with reference to FIG. 5.

The control device 50 comprises, as shown schematically in FIG. 1, a motor controller 51 for providing a control signal for the operation of the electric motor 14, and a control circuit 52 for implementing the control loops for controlling the centrifugal fan 10. The motor controller 51, such as a BLDC controller, is preferably arranged directly on the electric motor 14, in order to minimise electromagnetic interference (EMI). For the purpose of controlling the ventilation apparatus 100, the control circuit 52, such as an Arduino microcontroller, is preferably located directly on the centrifugal fan 10, in order to minimise the interfaces to the sensors and actuators.

The ventilation apparatus 100 is furthermore provided with an electrical interface 102 (see FIG. 1), which is configured for connecting at least one electrical connection for energy supply and for data exchange, and/or for a wireless connection of the ventilation apparatus 100 to an external network or control apparatus. The interface 102 is adapted for example for a 4-pole cable (2 poles for supply voltage, e.g. 12 V, and 2 poles for a USB port), and is adapted having an interface for the $SpO_2$ sensor, an interface for an optical and/or acoustic alarm, and a Bluetooth interface for remote control and/or a datalogger, e.g. having a computer or Smartphone.

In the following, the pneumatic configuration of the centrifugal fan 10 is described, which operates as a pressure generator for generating a flow-independent ventilation pressure of e.g. 5 mbar to 30 mbar. In the case of the centrifugal fan 10, comprising straight, radially extending fan blades 15, the ventilation pressure at the outlet opening of the centrifugal fan 10 generally results according to $$p=½*\rho*(2*p_i*f)^2*(r_a^2-r_i^2)$$

wherein: ρ=air density, f=rotational speed, $r_a$=outside diameter of the impeller, $r_i$=inside diameter of the impeller. In the case of a maximum rotational speed, achieved using a BLDC motor, of 40,000 rpm (670 Hz), a minimum outside diameter of approximately 40 mm results. In order to be able to achieve a flow of e.g. 100 l/min, the fan blades 15 preferably have a height of approximately 4 mm at the periphery. With the fan housing 13, a size of the centrifugal fan 10 of approximately 60 mm diameter and approximately 15 mm height results, at a mass of approximately 20 g. The dead volume of the centrifugal fan 10 is only approximately 10 ml.

These parameters, given by way of example, result in an average power P according to P=0.001 $m^3$/s*2,500 Pa=2.5 W. With an assumed efficiency of the ventilation apparatus 100 of 25%, the average power input into the electric motor 14 of from approximately 10 W to 12 W results. A motor of this power class weighs approximately 10 g and has a diameter of approximately 18 mm and a length of approximately 15 mm. A form factor of the fan (diameter>>length) allows for the integration of the fan, the measuring path for the flow measurement and the pressure measurement, the motor controller, and the expiration valve in a spherical housing 101 of the size of a tennis ball and having a mass of approximately 50 g. This advantageously achieves comparable sizes as in the case of a respiration gas filter of the Pall Ultipor 50 type, which has a mass of 26 g (dry) and 35 ml dead volume.

Figure 4:
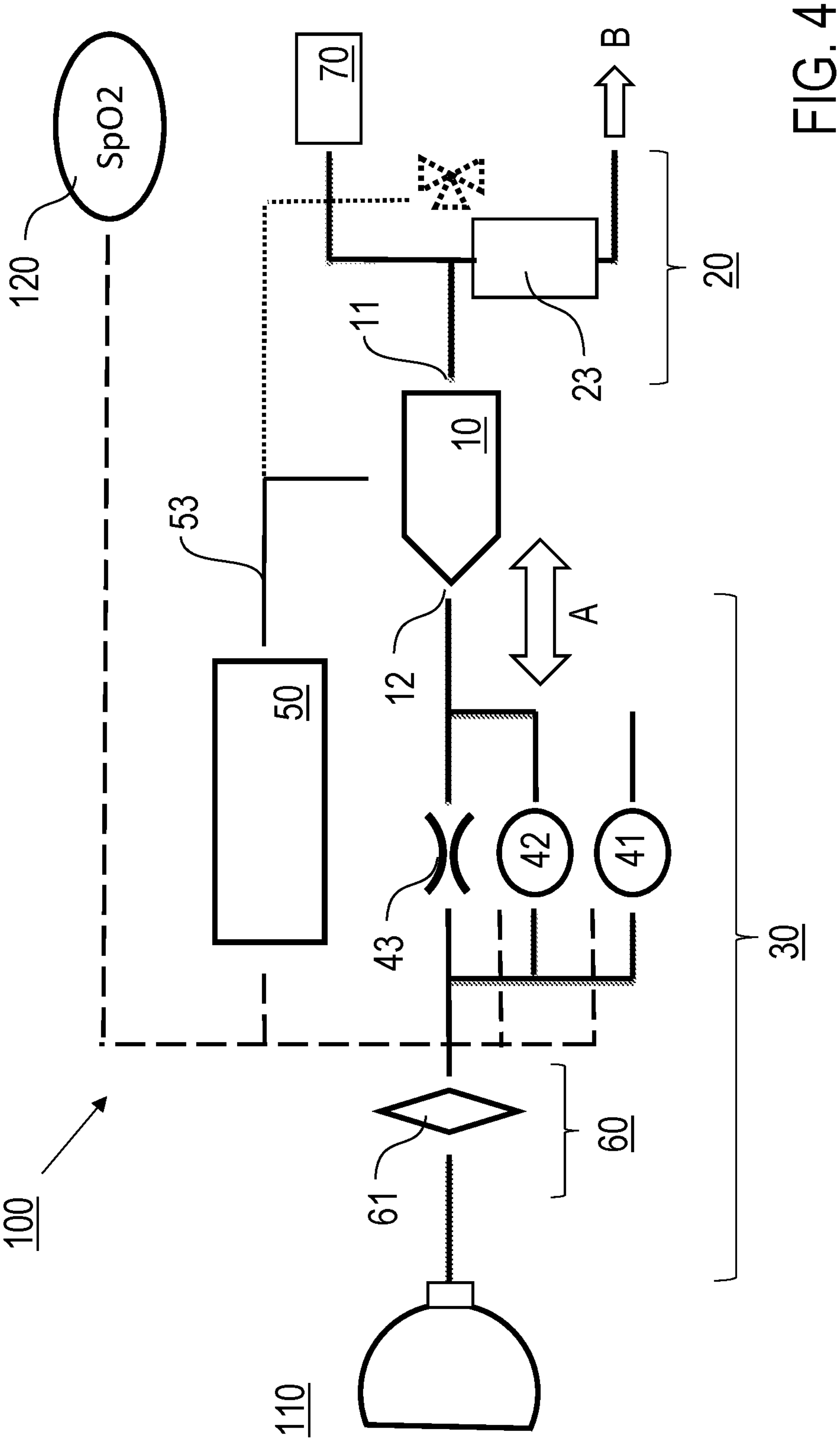
FIG. 4 is a flow diagram of the ventilation apparatus according to preferred embodiments of the invention.

The flow diagram according to FIG. 4 schematically illustrates the pneumatic and electrical configuration of the ventilation apparatus 100 with the centrifugal fan 10, the first and second respiration lines 20, 30, the sensor device 40, the control device 50, the filter device 60, and the respiration air conditioning device 70. The pneumatic interfaces of the centrifugal fan 10 comprise the inlet opening 11 having a hose connection for the air supply and having the expiration valve of the valve device 23, and the outlet opening 12 which opens towards the sensor device 40 and the filter device 60. The continuous bidirectional flow path (see double arrow A) is formed, on which air flows either towards the face mask 110 or in the reverse direction into the surroundings (arrow B).

The filter device 60 is arranged in the second respiration line 30, between the sensor device 40 and the face mask 110. The filter device 60 comprises a preferably replaceable HEPA filter 61. The HEPA filter 61 is preferably positioned directly on the face mask 110, such that advantageously the dead volume of the ventilation apparatus 100 is minimised.

For the purpose of humidification, temperature control and adjustment of the oxygen content of the respiration air, the respiration air conditioning device 70 is provided at the second end 21 of the first respiration line 20. The respiration air conditioning device 70 is located outside of the housing 101 of the ventilation apparatus 100 (see FIG. 1). In the respiration air conditioning device 70, inhalation air from the surroundings, optionally enriched with oxygen from an oxygen bottle, flows over heat exchangers from a resistance heating element and/or a Peltier element. Furthermore, the respiration air conditioning device 70 contains a humidifier, which loads the inhalation air with water vapour and/or aqueous aerosol droplets.

The pressure sensor 41 and the flow sensor 42 of the sensor device 40, as well as the oxygen saturation sensor 120, are connected via signal lines (shown dashed) to the control device 50, in particular the control circuit 52. During operation of the ventilation apparatus 100, the oxygen saturation sensor 120, e.g. a pulse oximeter, is coupled to the person to be ventilated, in order to acquire the oxygen saturation in the blood. The control device 50 is connected to the centrifugal fan 10, in particular the motor controller 51 thereof, via a control line 53. If, instead of the passive expiration valve, an actively actuatable three-way valve of the valve device 23 is provided, this is also actuated by means of the control device 50 (see dotted control line), in order to open alternately into one of the two branches of the first respiration line 20, according to the breathing rhythm. Optionally, the respiration air conditioning device 70 can also be actuated using the control device 50 or using an external controller.

The diameter of the first and second respiration lines is e.g. 15 mm. The length of the second respiration line 30 from the centrifugal fan 10 to the filter device 60 is e.g. 30 mm. At the narrowing 43, the second respiration line 30 has a diameter of e.g. 8 mm.

In a manner deviating from FIG. 4, the valve device 23 may be arranged having the valve opening to the surroundings on the side of the second respiration line 30, e.g. at the face mask 110 or between the sensor device 40 and the centrifugal fan 10. In this case, the first respiration line 20 preferably has one single branch only. If the expiration is intended to be pressure-controlled, however, the centrifugal fan 10 must be arranged on the mask side, before the expiration exit.

The compact design of the ventilation apparatus 100 illustrated in FIG. 4 offers in particular the following advantages. A hose system is not required, since the centrifugal fan 10, together with the sensor device 40, can be plugged directly onto the HEPA filter 61. Valves are not necessarily required. In particular an external expiration valve, as is conventional in the case of one-hose systems, is not required. The rest resistance of the ventilation apparatus 100 is in the order of magnitude of that of the HEPA filter, e.g. approximately 3 mbar*s/l. Since the pneumatic system can be temperature-controlled to temperatures of over 40° C. within a few seconds, condensation can be effectively prevented. An air stream used for system cooling can even be used with a simple air hood for heating the connected HEPA filter. The mechanical structure of the ventilation apparatus 100, comprising the housing and the respiration lines, is simple, e.g. can be produced using 3D printing, from plastics material.

Figure 5:
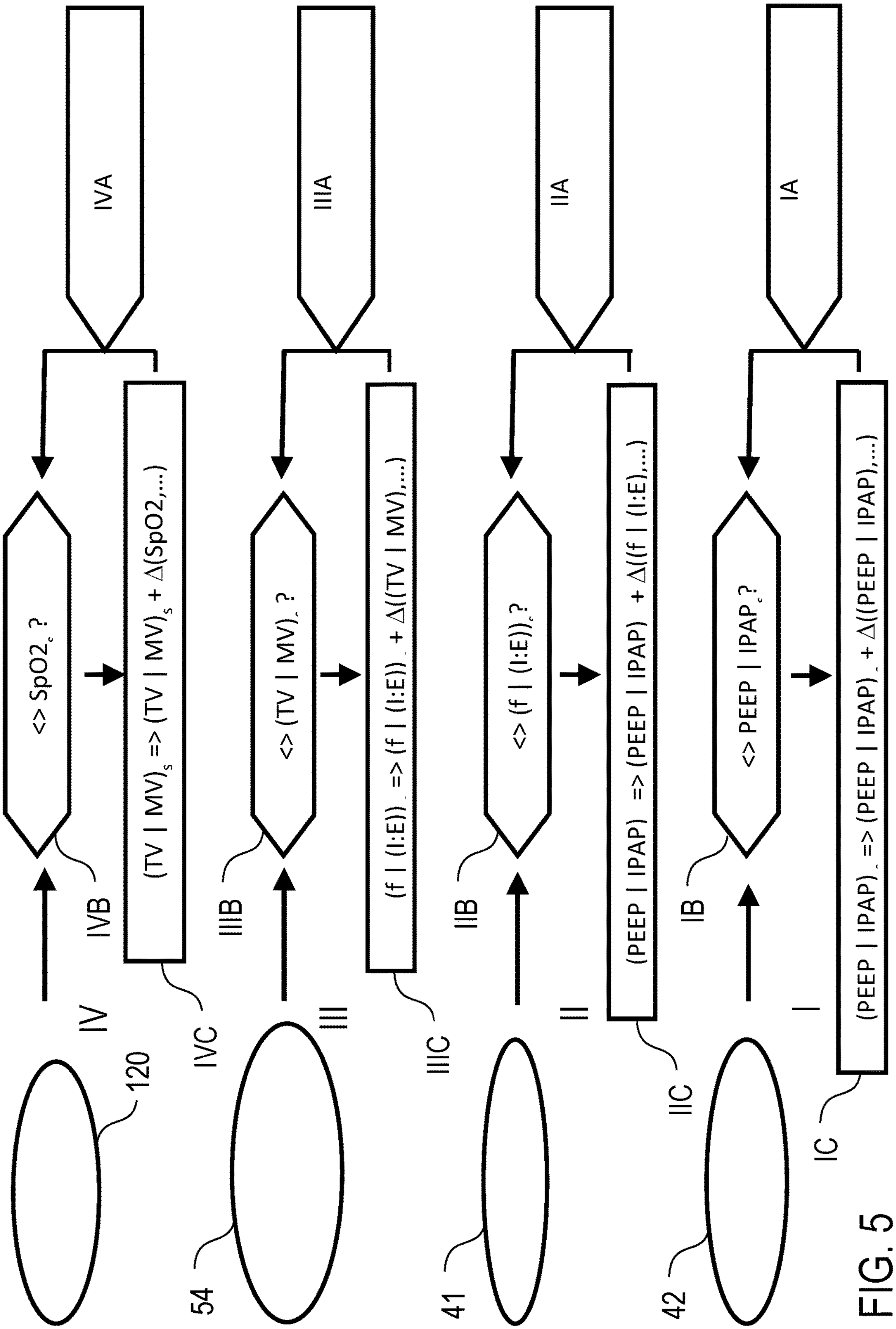
FIG. 5 is a flow diagram of a preferred embodiment of the control according to the invention of a centrifugal fan of a ventilation apparatus.

The ventilation pressure at the outlet opening 12 of the centrifugal fan 10 is adjusted alternately, using the multi-stage control method shown in FIG. 5, to an inhalation pressure or an exhalation pressure, as is explained in the following. The control method comprises four control loops I to IV, of which the first (I) and the second (II) control loop are necessary for the operation of the ventilation apparatus 100, while the third (III) and the fourth (IV) control loop are provided according to preferred embodiments of the invention. The control loops form a cascade, in which each control loop manipulates the target values of the control loop of the next-lowest level.

Actual values (reference variables) of the control loops are delivered in each case by the pressure sensor 42 for the first control loop I, the flow sensor 42 for the second control loop II, an output 54 of the control circuit 52 for the third control loop III, and the oxygen saturation sensor 120 for the fourth control loop IV. Limiters, denoted IA to IVA are provided in the control loops in each case, which limiters keep the control loops within specified limit values of time and pressure parameters. In the case of the test steps IB to IVB, predetermined target values are compared with the actual values, as is explained below. The “A” function calculates, in steps IC to IVC, the change in the respective controller target value on the basis of the pre-set parameters.

The first (innermost) control loop I comprises a pressure control, by means of which the ventilation pressure (inhalation pressure IPAP and exhalation pressure) is adjusted, using predetermined PIP and PEEP parameters (IA) as upper and lower limit values, respectively. The upper limit value PIP is selected by the treating operator, e.g. a doctor, such that the lung is not overexpanded during ventilation, and the lower limit value PEEP is selected such that the alveolae do not fall together upon exhalation. The PEEP parameter is preferably selected in the range of 5 mbar to 15 mbar, e.g. 8 mbar. The first control loop I is a PI controller, by means of which the ventilation pressure is adjusted using the rotational speed of the centrifugal fan 10, and the integration constants of which are given by the PIP and PEEP parameters.

At rest, a healthy person requires a respiration volume of approximately 8 ml air/(kg [body weight]*min). In general, the state of the patient will change over time, e.g. an improvement in the phase of weaning off the ventilating, or a worsening e.g. on account of advancing atelectasis (alveolar collapse). In order to prevent the collapse of the alveolae at the end of the expiration phase, it is provided for the minimum pressure (PEEP, positive end-expiratory pressure) to be maintained. Accordingly, the ventilation apparatus 100 has to generate only varying positive pressures.

The next highest level comprises, with the second control loop II, a time control, the target values of which for frequency (f) of the inhalation and duty cycle of inhalation and exhalation (I:E) are adjusted (in a parameterisable manner) within physiologically reasonable limits. Together with the subordinate pressure control, the BIPAP functionality is already implemented. The frequency is selected for example in the range of from 25 $min^{-1}$ to 12 $min^{-1}$. The duty cycle is selected for example in the range of from 30% (at low frequencies) to 50% (at high frequencies).

At the second-lowest level the third control loop III implements a control of the tidal and/or minute volume (TV, MV), in order to be able to react to changes in the stiffness of the lungs and the airway resistance within specified limits (parameterizable). The reference variable is the tidal volume which is calculated by the temporal integration of the measured flow during inspiration and expiration phases, and is provided by the control circuit 52 at the output 54. The target value for the third control loop III is specified by the minute volume parameter. The output of the third control loop III modifies the target value specifications of the pressure control of the first control loop I and the time control of the second control loop II.

At the highest level, the fourth control loop IV specifies the target value of the minute volume by an i-controller, which has the oxygen saturation as the reference variable and compares this with its local target value. As a result, the entire control loop is closed. Too low an oxygen saturation for examples leads to a gradual increase in the minute volume specification, and this leads to an increase in the target values for PIP, breath frequency, inspiration/expiration ratio, and PEEP.

The limits of the ranges of all target values are parameterised. Thus, the controls of the individual control loops, in the absence of a reference variable or control variable of a higher level, automatically remain in the range of that which is specified by the local parameterisation thereof. A failure of the oxygen saturation sensor 120 would lead for example to freezing of the target value for the minute volume and, in the case of activated control in the fourth control loop IV, would lead to a warning. If desired minute volumes cannot be achieved within the specified limits of the time control or pressure control, e.g. on account of too high a compliance, the system automatically remains within these limits and issues a warning.

During operation of the ventilation apparatus 100, preferably at least one of the following safety measures is provided. In the case of a power failure, the behaviour of the ventilation apparatus 100 transitions into that of an FFP3 mask. The maximum rotational speed of the centrifugal fan 10, and thus the achievable system pressure, are fixed in an invariable manner by the fan design, the operating voltage, and the diameter of the fan wheel. A failure of the motor controller 51 cannot lead to a motor wearing out, and a blow out as in the case of DC motors is not possible. There are no blocking valves; inhalation and exhalation airways are always completely open and are only dynamically pressurised. Non-ventilated masks can thus be used without limitation. After a short warming phase, formation of condensate is prevented by the design, inter alia on account of the lack of hose lines.

There are at least two possibilities in order to be able to estimate possible losses by leakage of the face mask during NIV ventilating. Firstly, a measurement and extrapolation of the flow and pressure data at the end of the inspiration phase results in an estimation of the flow caused by mask leakages, at a constant pressure. Secondly, a bidirectional measurement of the flow in front of the centrifugal fan can be provided.

In summary, the ventilation apparatus 100 advantageously has at least one of the following features. The ventilation apparatus 100 ensures that the ventilated person obtains enough oxygen (oxygen saturation typically >90%), and that enough $CO_2$ is removed in order to maintain their vital functions. The system is adapted to acquire the reference variable oxygen saturation ($SpO_2$). Additional oxygen can be fed in. The ventilation apparatus 100 can autonomously compensate for changes in the lung condition of the ventilated person, within physiologically reasonable limits, by changing the tidal or minute volume. The ventilation apparatus 100 can signal to the clinicians, via acoustic, optical and/or digital alarms, when there is a risk of the treatment destabilising.

The features of the invention disclosed in the above description, the drawings, and the claims, can be of significance both individually and in combination or sub-combination for implementing the invention in the various embodiments thereof.

The invention claimed is:

1. A ventilation apparatus which is adapted for non-invasive ventilating of a person, comprising:

a centrifugal fan having an inlet opening and an outlet opening, the centrifugal fan being adapted to receive ventilation air at the inlet opening and to provide the ventilation air at an adjustable ventilation pressure at the outlet opening, a first respiration line having a first end connected to the inlet opening of the centrifugal fan, and having a second end arranged for receiving inhalation air, a second respiration line having a first end connected to the outlet opening of the centrifugal fan, and having a second end adapted for coupling a ventilation mask, the second respiration line being provided with a sensor device, by means of which at least one flow parameter in the second respiration line can be measured, and a control device adapted for controlling the centrifugal fan in dependency on at least one output signal of the sensor device, wherein the centrifugal fan and the second respiration line form a continuous bidirectional flow path, the adjustable ventilation pressure at the outlet opening of the centrifugal fan comprising an inhalation pressure or an exhalation pressure which is equal to or less than the inhalation pressure, and the second respiration line is provided with a filter device which is arranged for air flow filtering;

the first respiration line includes a valve device arranged between the inlet opening of the centrifugal fan and the second end of the first respiration line and arranged as an expiration exit for the outlet of exhalation air.

2. The ventilation apparatus according to claim 1, wherein:

the flow path between the second end of the second respiration line and the inlet opening of the centrifugal fan is free of valves.

3. The ventilation apparatus according to claim 1, wherein:

the valve device is a passive outlet valve.

4. The ventilation apparatus according to claim 1, wherein:

the second end of the first respiration line opens into surroundings of the ventilation apparatus.

5. The ventilation apparatus according to claim 1, wherein:

the second end of the first respiration line is adapted for coupling to a respiration air reservoir.

6. The ventilation apparatus according to claim 1, comprising:

a respiration air conditioning device which is coupled to the second end of the first respiration line.

7. The ventilation apparatus according to claim 6, wherein:

the respiration air conditioning device is adapted for adjusting at least one of the parameters moisture, temperature and oxygen content of the inhalation air.

8. The ventilation apparatus according to claim 7, wherein:

the respiration air conditioning device comprises a temperature control device which is adapted for controlling the temperature of the ventilation apparatus.

9. The ventilation apparatus according to claim 1, having at least one of the features:

the filter device comprises a HEPA filter, and the filter device comprises a plug connection to at least one of the centrifugal fan and the second respiration line.

10. The ventilation apparatus according to claim 1, having at least one of the features:

the control device is provided with an interface for receiving an output signal of an oxygen saturation sensor, the control device is arranged directly adjoining the centrifugal fan, and the control device is adapted for outputting an alarm signal in the event of at least one of a malfunction of the ventilation apparatus and a critical state of the ventilated person being identified.

11. The ventilation apparatus according to claim 1, wherein:

the control device is adapted for controlling the centrifugal fan using a first control loop, by means of which the ventilation pressure at the outlet opening of the centrifugal fan can be adjusted.

12. The ventilation apparatus according to claim 11, wherein:

the control device is adapted for controlling the centrifugal fan using a third control loop, by means of which target variables of the first control loop are adjustable in such a way that at least one of the parameters of tidal volume and minute volume of the ventilation can be matched to predetermined volume reference variables of the tidal volume or of the minute volume.

13. The ventilation apparatus according to claim 12, wherein:

the control device is adapted for controlling the centrifugal fan in dependency on an output signal of an oxygen saturation sensor using a fourth control loop, by means of which a target variable of the third control loop is adjustable such that an oxygen saturation in the blood of the ventilated person is matched to a predetermined oxygen saturation reference variable.

14. The ventilation apparatus according to claim 1, wherein:

the control device is adapted for controlling the centrifugal fan using a second control loop, by means of which at least one of the following can be adjusted: a frequency of inhalation phases, in which the inhalation pressure is established at the outlet opening of the centrifugal fan, and a duty cycle of the duration of the inhalation phases relative to the duration of exhalation phases, in which the exhalation pressure is established at the outlet opening of the centrifugal fan.

15. The ventilation apparatus according to claim 14, wherein:

the control device is adapted for controlling the centrifugal fan using a third control loop, by means of which target variables of the second control loop are adjustable in such a way that at least one of the parameters of tidal volume and minute volume of the ventilation can be matched to predetermined volume reference variables of the tidal volume or of the minute volume.

16. The ventilation apparatus according to claim 15, wherein:

the control device is adapted for controlling the centrifugal fan in dependency on an output signal of an oxygen saturation sensor using a fourth control loop, by means of which a target variable of the third control loop is adjustable such that an oxygen saturation in the blood of the ventilated person is matched to a predetermined oxygen saturation reference variable.

17. A control method for controlling a centrifugal fan for ventilating a person, comprising at least one of the steps of:

controlling the centrifugal fan using a first control loop, by means of which the ventilation pressure at an outlet opening of the centrifugal fan can be adjusted to an inhalation pressure or an exhalation pressure which is equal to or less than the inhalation pressure, and controlling the centrifugal fan using a second control loop, by means of which at least one of the following can be adjusted: a frequency of inhalation phases, in which the inhalation pressure is established at the outlet opening of the centrifugal fan, and a duty cycle of a duration of the inhalation phases relative to a duration of exhalation phases, in which the exhalation pressure is established at the outlet opening of the centrifugal fan;

wherein the centrifugal fan includes an inlet opening and an outlet opening, the centrifugal fan being adapted to receive ventilation air at the inlet opening and to provide the ventilation air at an adjustable ventilation pressure at the outlet opening, and the centrifugal fan is included in a ventilation apparatus comprising:

a first respiration line having a first end connected to the inlet opening of the centrifugal fan, and having a second end arranged for receiving inhalation air, a second respiration line having a first end connected to the outlet opening of the centrifugal fan, and having a second end adapted for coupling a ventilation mask, the second respiration line being provided with a sensor device, by means of which at least one flow parameter in the second respiration line can be measured, and a control device adapted for controlling the centrifugal fan in dependency on at least one output signal of the sensor device, wherein the centrifugal fan and the second respiration line form a continuous bidirectional flow path, the adjustable ventilation pressure at the outlet opening of the centrifugal fan comprising an inhalation pressure or an exhalation pressure which is equal to or less than the inhalation pressure, and the first respiration line includes a valve device arranged between the inlet opening of the centrifugal fan and the second end of the first respiration line and arranged as an expiration exit for the outlet of exhalation air;

the second respiration line is provided with a filter device which is arranged for air flow filtering;

wherein the control device is adapted for controlling the centrifugal fan using a second control loop, by means of which at least one of the following can be adjusted: a frequency of inhalation phases, in which the inhalation pressure is established at the outlet opening of the centrifugal fan, and a duty cycle of the duration of the inhalation phases relative to the duration of exhalation phases, in which the exhalation pressure is established at the outlet opening of the centrifugal fan;

wherein the control device is adapted for controlling the centrifugal fan using a third control loop, by means of which target variables of the second control circuit are adjustable in such a way that at least one of the parameters of tidal volume and minute volume of the ventilation can be matched to predetermined volume reference variables of the tidal volume or of the minute volume; and wherein the control device is adapted for controlling the centrifugal fan in dependency on an output signal of an oxygen saturation sensor using a fourth control loop, by means of which a target variable of the third control loop is adjustable such that an oxygen saturation in the blood of the ventilated person is matched to a predetermined oxygen saturation reference variable.

18. The control method according to claim 17 further comprising the steps of:

operating the centrifugal fan;

measuring the at least one flow parameter using the sensor device.

* * * * *